(12) United States Patent
Ball

(10) Patent No.: US 10,315,037 B2
(45) Date of Patent: Jun. 11, 2019

(54) ADAPTING TO WIRELESS PROXIMAL COMMUNICATION SIGNAL DISTORTION BETWEEN DEVICES

(71) Applicant: MEDTRONIC, INC., Minneapolis, MN (US)

(72) Inventor: Warren Ball, Coon Rapids, MN (US)

(73) Assignee: MEDTRONIC, INC., Minneapolis, MN (US)

( * ) Notice: Subject to any disclaimer, the term of this patent is extended or adjusted under 35 U.S.C. 154(b) by 328 days.

(21) Appl. No.: 14/603,610

(22) Filed: Jan. 23, 2015

(65) Prior Publication Data

US 2016/0213935 A1 Jul. 28, 2016

(51) Int. Cl.
*A61N 1/372* (2006.01)
*A61N 1/378* (2006.01)

(52) U.S. Cl.
CPC ...... *A61N 1/37211* (2013.01); *A61N 1/37252* (2013.01); *A61N 1/3787* (2013.01); *A61N 1/37223* (2013.01)

(58) Field of Classification Search
CPC .......................... A61N 1/37252; A61N 1/3727
See application file for complete search history.

(56) References Cited

U.S. PATENT DOCUMENTS

| 5,843,139 A | 12/1998 | Goedeke |
| 6,738,670 B1 | 5/2004 | Almendinger |
| 2005/0131494 A1* | 6/2005 | Park ..................... A61N 1/3727 607/60 |
| 2014/0012341 A1 | 1/2014 | Von Arx |
| 2014/0025139 A1* | 1/2014 | Stouffer ............. A61N 1/37223 607/60 |

\* cited by examiner

*Primary Examiner* — George R Evanisko
(74) *Attorney, Agent, or Firm* — Withers & Keys, LLC

(57) ABSTRACT

Devices that communicate using wireless proximal communications measure pulse width to find distortion in the received signal. The distortion may be due to the devices being too close to one another for a transmission power level currently being used which causes ringing of a receiving coil. The distortion may be used to find a correction that the receiving device may use to correct for the distortion in the received pulse train when decoding the pulse train. The distortion may be used to adjust a transmission power level of the receiving device and/or to send an instruction to the transmitting device to adjust the power transmission power level of the transmitting device. The distortion may be used for other purposes including determining a device depth and/or location for an implanted device, such as an implantable medical device within a body of a patient.

20 Claims, 15 Drawing Sheets

ADAPTING TO WIRELESS PROXIMAL COMMUNICATION SIGNAL DISTORTION BETWEEN DEVICES

TECHNICAL FIELD

Embodiments relate to devices that communicate using wireless proximal communication signals. More particularly, embodiments relate to adapting to distortion of the wireless proximal communication signal being communicated between the devices.

BACKGROUND

Devices use wireless proximal communications to exchange information. For example, an external programmer device may communicate with an implantable medical device using wireless proximal communications in order to send therapy programming to the implantable medical device and/or to obtain physiological or other data from the implantable medical device.

The wireless proximal communication signals typically have a relatively short range of a few feet or less and rely on close proximity of the two devices in order to establish the communication link. The close proximity of the two devices provides an assurance that the two intended devices are the devices that are actually communicating with one other. An example of wireless proximal communication signals utilizes inductive coupling to transfer the signals and is often referred to as near field communications.

While the proximity of the two devices enables the communication link to be achievable and aids in assuring the two intended devices are in communication, the close proximity may result in the received signal being distorted. If the power level of the signal being received is excessive for the distance separating the two devices that are communicating, then the wireless proximal signal may cause the receiving coil of the receiving device to ring. The ringing of the receiving coil results in distortion that may be at a level that causes difficulty and errors when attempting to decode the pulse train of the received signal.

SUMMARY

Embodiments address issues such as these and others by adapting to the distortion. For instance, the distortion may be measured to find a correction, and then the correction is applied to the received pulse train prior to decoding the pulse train. In another example, the distortion may be measured by the receiving device and then the sending device may be instructed as to a reduction in transmission power to reduce the distortion occurring at the receiving device. As another example, the receiving device may measure the distortion in order to control its own transmission power to reduce distortion occurring in the signal being received at the other device. Other uses for measuring the distortion include using the change in distortion due to a change in distance between devices to allow the location of a device to be determined, such as determining where an implantable medical device is located and whether it has migrated over time. Another example includes determining a depth of a device, such as the depth of an implantable medical device within a patient, based on the amount of distortion that is measured which may also indicate device migration.

Embodiments provide a method of exchanging wireless proximal communications that involve receiving at a first device a wireless signal that includes a header portion representing header data and a body portion representing body data. The method further involves obtaining header pulses representative of the header data and body pulses representative of the body data from the received wireless signal, where the header pulses have a header pulse width and the body pulses have a body pulse width. The method also involves determining a correction based on the header pulse width and applying at the first device the correction when decoding the data represented by the body pulses.

Embodiments provide a device for exchanging wireless proximal communications that includes a receiving circuit that receives and demodulates a wireless signal that includes a header portion and that includes a body portion to produce a demodulated signal of the header portion and the body portion. The device also includes a processor that converts the demodulated signal to pulses of the header portion and the body portion with the pulses having a pulse width, determines a correction based on the header pulse width, and applies the correction when decoding the body data.

Embodiments provide a system for exchanging wireless proximal communications that includes a first device and a second device. The first device includes a receiving circuit that receives and demodulates a first wireless signal that includes a header portion and that includes a body portion to produce a demodulated signal of the header portion and the body portion. The first device also includes a processor that converts the demodulated signal to pulses of the header portion and the body portion with the pulses having a pulse width, determines a correction based on the header pulse width, and applies the correction when decoding body data from the body pulses. The first device further includes a transmitter circuit that transmits a second wireless signal. The second device includes a receiving circuit that receives and demodulates the second wireless signal that includes a header portion and that includes a body portion to produce a demodulated signal of the header portion and the body portion. The second device also includes a processor that converts the demodulated signal to pulses of the header portion and the body portion of the second wireless signal with the pulses having a pulse width, determines a second correction based on the header pulse width, and applies the second correction when decoding body data from the body pulses. Additionally, the second device includes a transmitter circuit that transmits the first wireless signal.

Embodiments provide a method of controlling transmission power of a first device that communicates through a wireless proximal connection that involves receiving a wireless signal from a second device through a telemetry head at a reference position. The method further involves obtaining pulses having a pulse width from the received wireless signal and adjusting the transmission power of the first device based on the pulse width.

Embodiments provide a method of detecting an implantation depth of an implanted device that communicates through a wireless proximal connection that involves receiving a wireless signal from the device through a telemetry head at a reference position. The method further involves obtaining pulses having a pulse width from the received wireless signal and determining the depth of the implanted device from the pulse width.

Embodiments provide a method of locating a position of a first device that communicates through a wireless proximal connection. The method includes, while a telemetry head connected to a second device is moving, receiving at the second device a wireless signal from the first device through the telemetry head and obtaining at the second device a train of pulses with each having a pulse width from the received wireless signal. The method further includes comparing at the second device the pulse width of one pulse at a reference position within the pulse train to the pulse width of a prior occurring pulse of a prior pulse train at the reference position. When the pulse width of the one pulse is greater than the pulse width of the prior occurring pulse, the method involve providing an annunciation from the second device that indicates the telemetry head is now closer to the first device. When the pulse width of the one pulse is less than the pulse width of the prior occurring pulse, the method involves providing an annunciation from the second device that indicates the telemetry head is now further from the first device.

Embodiments provide a method of controlling transmission power of a first device that communicates through a wireless proximal connection with a second device. The method involves receiving a wireless signal at the second device and obtaining pulses having a pulse width from the received wireless signal. The method further involves determining information related to an adjustment of the transmission power of the first device based on the pulse width, and sending the information related to the adjustment of the transmission power of the first device to the first device via a second wireless signal.

DETAILED DESCRIPTION

Embodiments determine distortion within a received wireless proximal signal for various purposes. For instance, the distortion may be used to determine a correction to be applied to received signals to improve the accuracy of the decoding process. The distortion may be used to adjust the transmission power of the device determining the distortion of the received signal or to instruct the transmitting device as to transmission power. The distortion may be used to determine the depth and/or position of an implanted device.

Figure 1:
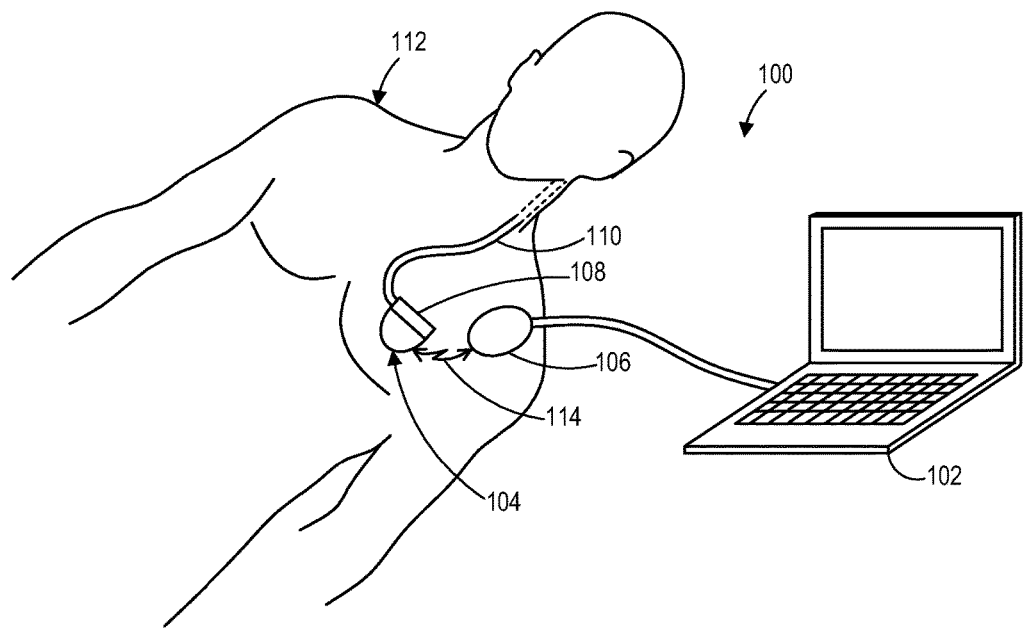
FIG. 1 shows an example of wireless proximal communications between devices where signal distortion may be corrected and/or used for other purposes.

FIG. 1 shows an example of an operating environment for the various embodiments. A system 100 includes a first device 102 such as an external programmer that has a telemetry head 106 that exchanges wireless proximal signals 114 with a second device 104 such as an implantable medical device (IMD). First device 102 may be any type of programmer (e.g., clinician and/or patient programmer), may alternatively or additionally serve as a recharger for recharging a power source of second device 104, may be a monitoring unit for monitoring status, or may be any other type of device capable of exchanging wireless proximal signals 114 with second device 104, including an off-the-shelf device such as a cell phone with such capability. In embodiments described below, first and second devices 102, 104 may be capable of only receiving wireless proximal signals 114, of only transmitting such signals, or capable of both. In an embodiment wherein the second device 104 is an IMD, the IMD (also referred to herein after as "IMD 104") may be implanted within a patient 112. While the label of first device has been applied to an external device and the label of second device has been referred to as an implantable device, it will be appreciated that the labels of first device and second device as used herein are generic and may also refer to an implantable device and an external device, respectively. In this particular example, the IMD 104 includes leads 110 that are routed to a target site within the patient 112 to provide electrical stimulation signals to the target site and/or to sense physiological signals at the target site.

Figure 2:
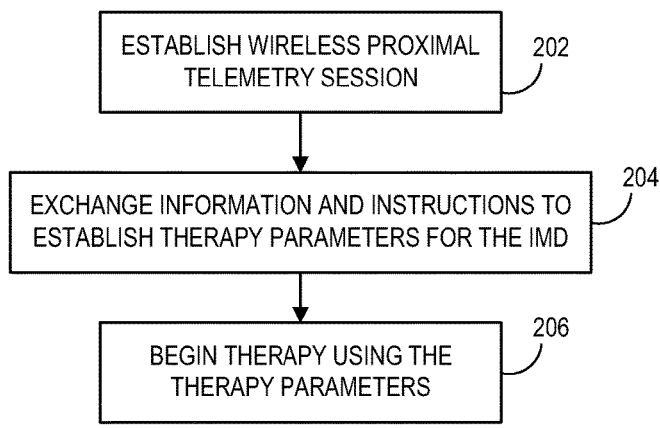
FIG. 2 shows an example of operations for the exchange of information between an external programmer device and an implantable medical device by using wireless proximal communications where signal distortion may be corrected and/or used for other purposes.

FIG. 2 shows an example of operations of the system 100. Initially, the devices 102, 104 communicate via the bi-directional signals 114 to establish a telemetry session at an operation 202. The 102, 104 devices then exchange information via the signals 114 at an operation 204. For example, the external programmer 102 may send instructions to the IMD 104 that specify therapy parameters for purposes of establishing stimulation therapy. The IMD 104 may send confirmation of the instructions, status information such as battery life remaining, and may send collected physiological data to the external device 102. The IMD 104 applies the programming that it has received to begin providing therapy with the specified therapy parameters at an operation 206.

Figure 3:
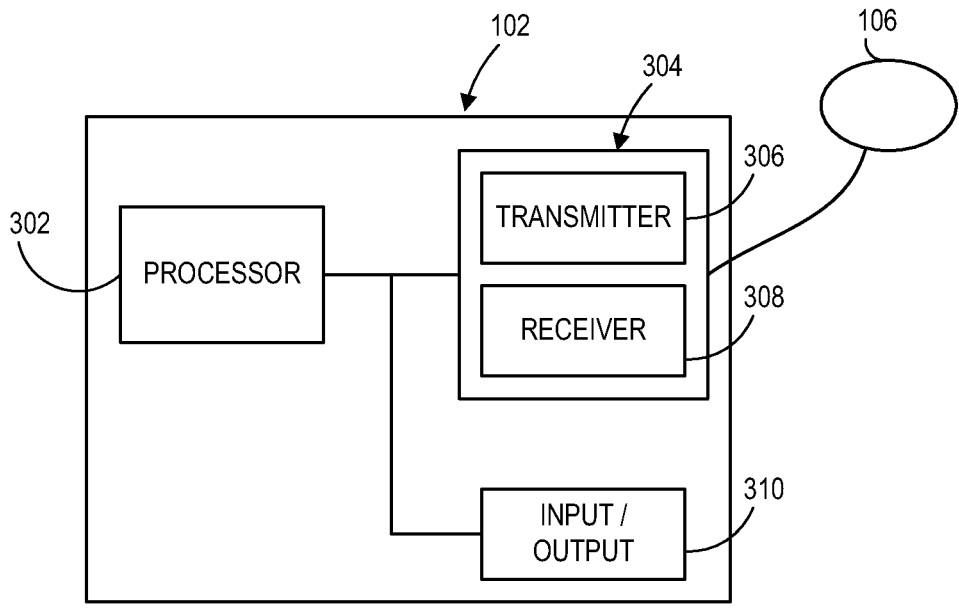
FIG. 3 shows an example of components of an external device that may utilize wireless proximal communication signals and may further make use of the measured distortion of those signals.

FIG. 3 shows an example of the first device 102. Several components of the first device 102 are contained within a housing. These include a processor 302 as well as a communication circuitry 304 and an input/output circuitry 310. The processor 302 interacts with the communication circuitry 304 and input/output circuitry 310 to provide the operations of the first device 102.

The processor 302 performs various logical operations when interacting with the other components. These operations may utilize distortion measured from a received wireless proximal signal in various ways. Examples of these logical operations are discussed below in relation to FIGS. 5-17. The processor 302 may be of various forms such as a general purpose programmable processor, application specific processor, hardwired digital logic, and/or various combinations.

The communication circuitry 304 includes both a transmitter circuit 306 and a receiver circuit 308 for sending and receiving signals in the wireless proximal frequency bands, typically with the carrier in the tens and hundreds of kilohertz. The transmitter circuit 306 may modulate a carrier by a pulse train encoding data while the receiver circuit 308 may demodulate the pulse train from the carrier to allow data to be decoded. Telemetry protocols such as amplitude shift keying (ASK) may be utilized for the pulse train. The communication circuitry 304 is tethered to the telemetry head 106 that includes at least one coil or other antenna design electrically coupled to the communication circuitry 304 for transmitting and/or receiving wireless proximal signals 114.

The input/output circuitry 310 allows the external device 102 to interact with users or other devices. The input/output circuitry 310 may provide outputs such as a visual display on a screen, audio, and the like. The input/output circuitry 310 may provide inputs such as a keyboard or keypad, a mouse and/or touch screen, and the like. The input/output circuitry 310 allows users to enter information such as programming details to be provided from the first device 102 to the second device 104 as well as review information such as physiological data sent from the second device 104 to the first device 102.

Figure 4:
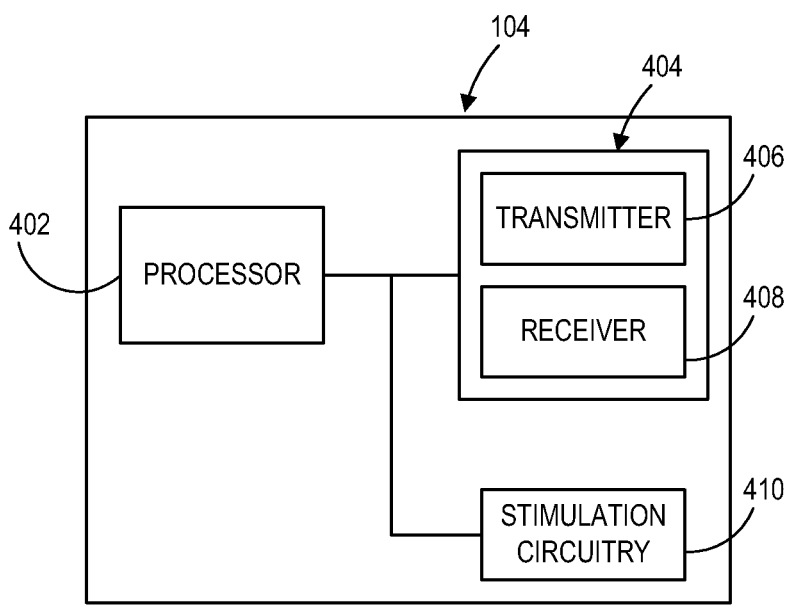
FIG. 4 shows an example of components of an implantable device that may utilize wireless proximal communication signals and may further make use of the measured distortion of those signals.

FIG. 4 shows an example of the second device 104. Several components of the second device 104 are also contained within a housing. For examples where the second device 104 is an implantable medical device, the housing containing these components is constructed of a biocompatible material that is hermetically sealed. The components of the second device 104 include a processor 402 as well as a communication circuitry 404. Where the second device 104 is a medical stimulation device, a stimulation circuitry 410 is also present. The processor 402 interacts with the communication circuitry 404 and stimulation circuitry 410 to provide the operations of the second device 104.

The processor 402 performs various logical operations when interacting with the other components. As the second device 404 may also measure distortion in a received signal, the second device 104 may perform the same operations performed by the first device 102 except for those operations that are useful to examine the depth or location of an implanted second device 104. Thus, examples of the logical operations of the second device are discussed below in relation to FIGS. 5-14. The processor 402 may be of various forms such as a general purpose programmable processor, application specific processor, hardwired digital logic, and/or various combinations.

The communication circuitry 404 includes both a transmitter circuit 406 and a receiver circuit 408 for sending and receiving signals in the wireless proximal frequency bands, typically in the tens and hundreds of kilohertz. The transmitter circuit 406 may modulate a carrier by a pulse train that encodes data while the receiver circuit 408 may demodulate the pulse train from the carrier to ultimately decode the data. In this example, an antenna such as a coil or other antenna design is included within the communication circuitry 404 and is within the same housing, rather than tethered to a telemetry head, for transmitting and/or receiving wireless proximal signals 114.

The stimulation circuitry 410 in the example shown allows the second device 104 to interact with the body of the patient 112. The stimulation circuitry 410 may provide stimulation therapy and/or collect physiological data. The circuitry 410 may be of other forms as well, such as a drug pump mechanism rather than a stimulator.

Figure 5:
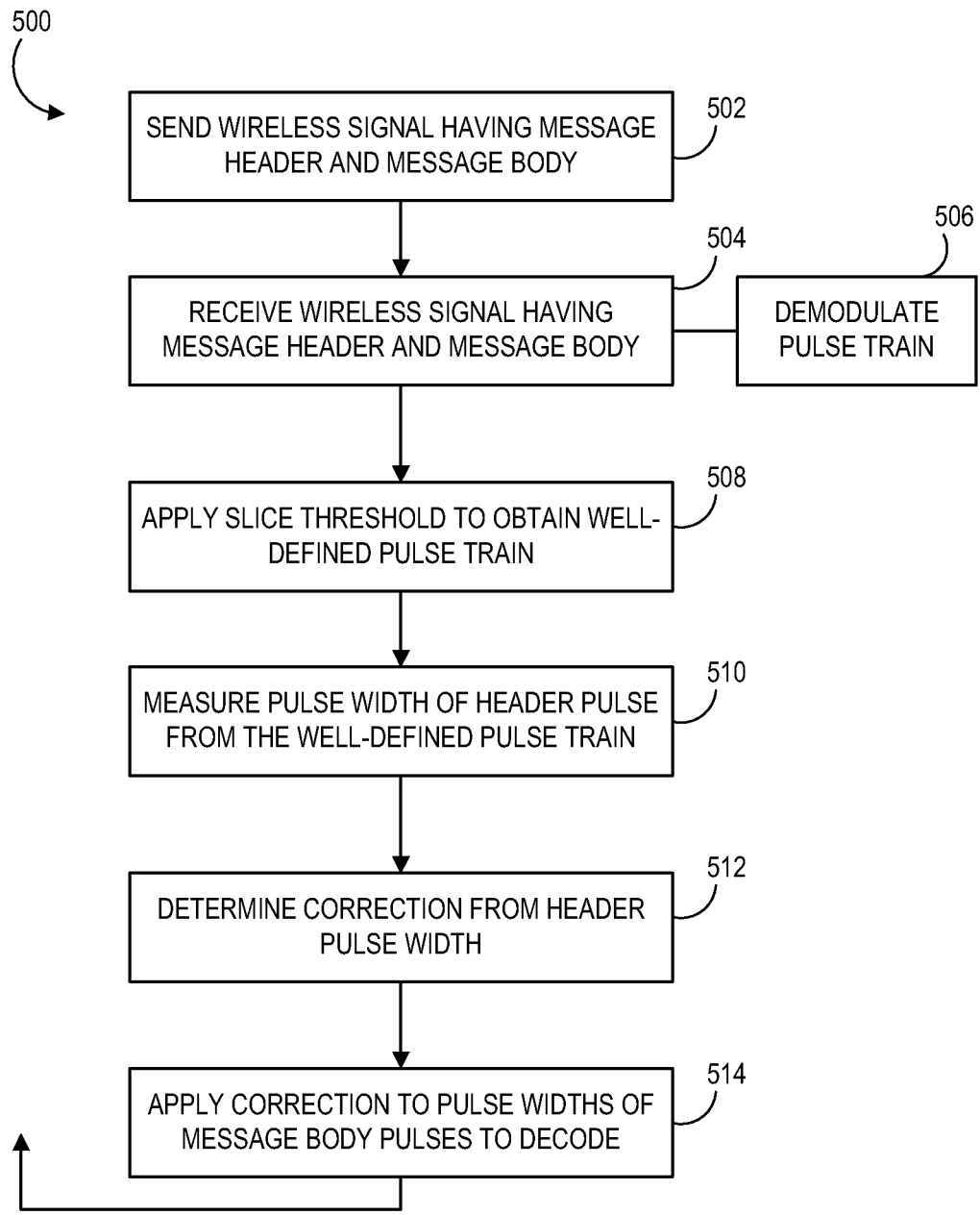
FIG. 5 shows an example of operations of a device to exchange wireless proximal communications and apply a correction.

Either the first device 102, the second device 102, or both devices may measure distortion in a wireless proximal signal being received for various purposes. FIG. 5 shows a set 500 of logical operations that may be performed by either or both devices 102, 104 in order to measure and correct for the distortion in the received signal. This correction may improve the accuracy of the decoding process that converts a pulse train extracted from the received signal into usable data.

The operations begin by one device sending a wireless proximal signal to the other device at an operation 502. The wireless proximal signal is then received at the other device at an operation 504. The wireless proximal signal of this example includes a header portion and a message body portion. An example of a header portion of such a signal as received without distortion is shown in a waveform diagram 700 of FIG. 7 as waveform 702. An example of a body portion of such a signal as received without distortion, which occurs in time after the header portion, is shown in a waveform diagram 800 of FIG. 8 as waveform 802. It will be appreciated that the duty cycle of these portions may vary from those shown. Furthermore, the duty cycle may vary from one reference pulse position to another and/or from the header portion to the body portion of a message in a wireless signal. For example, the duty cycle may be 50% where Manchester encoding is used for one or more of these portions of the messages but other duty cycles may be used for other encoding formats.

The header and body portions are demodulated at an operation 506 as they are being received such that the operation 506 may be performed as a sub-operation of the operation 504. This is shown by similar convention throughout the drawings. Examples of the demodulated pulse trains are shown as header pulse train 704 of FIG. 7 and body pulse train 804 of FIG. 8. Note that in this example, FIG. 8 is at a higher zoom factor than FIG. 7 such that the body portion can more clearly be inspected. The demodulated pulse train is then sliced using a threshold 706, 806 at an operation 508 to produce a well defined pulse train 708 for the header portion and pulse train 808 for the body portion that is suitable for decoding.

In this example, the width in time of at least certain pulse locations in the header portion of the pulse train 708, 808 are a known and fixed quantity, i.e., a fixed data rate, and therefore may serve as a reference for whether there is distortion. The body portion of the received signal may have a data rate that may vary from one message to the next, and that data rate may be specified by the header data so that the decoder can properly decode the body portion. Any distortion of the received signal due to ringing of the receiving coil, which may be caused by the devices being too close together for the power level being used to transmit the signal, will result in the header pulse in the reference position having an "on" time with a greater width than the reference quantity for the "on" time and consequently have an "off" time of less width than the reference quantity for the "off" time. Therefore, at an operation 510, the receiving device can measure the pulse width of the header pulse in the reference position to then determine if the pulse width, either the "on" time or the "off" time, is the same or different than the reference.

Figure 7:
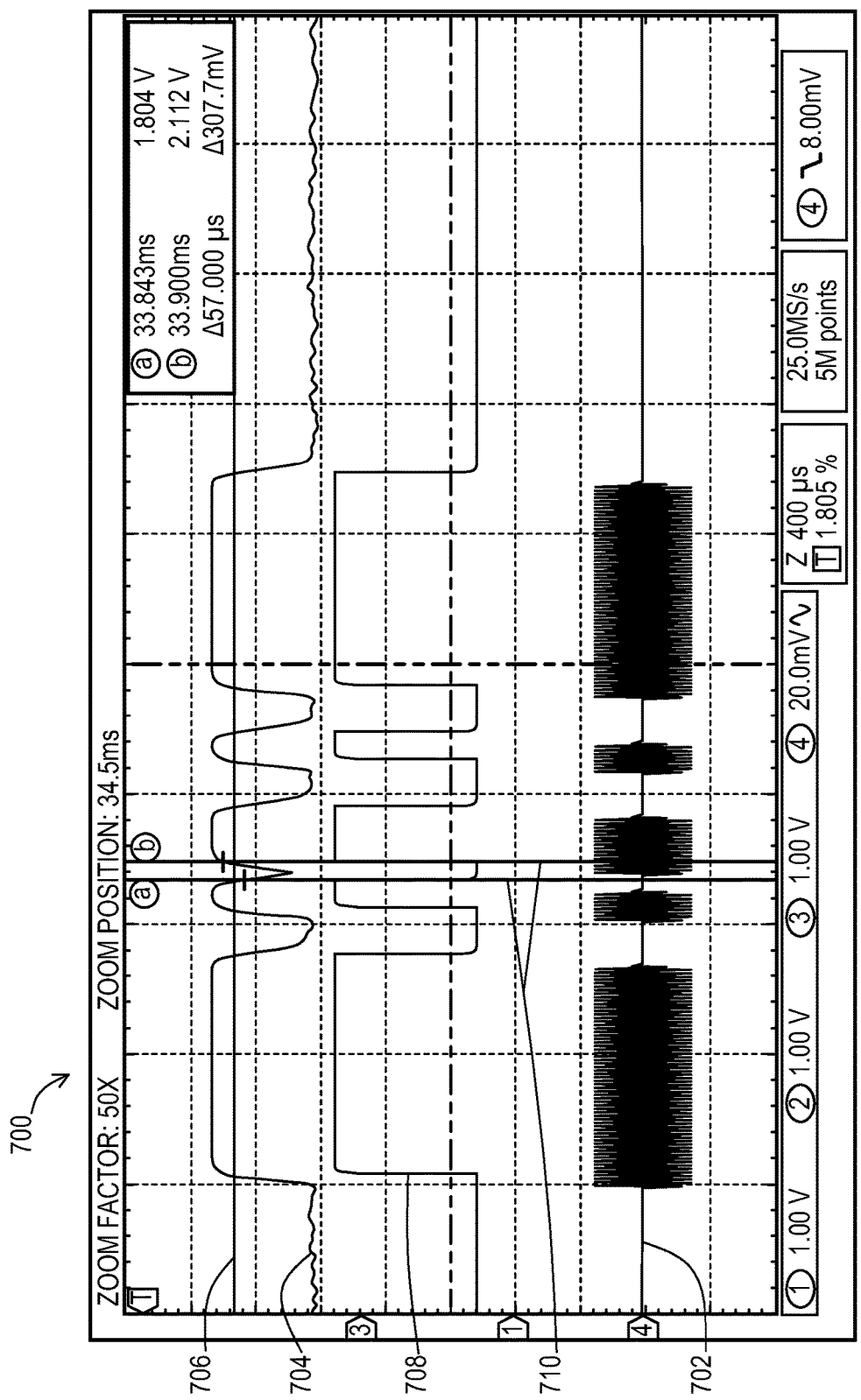
FIG. 7 shows the waveforms from a header portion of a transmitted wireless proximal signal and both undistorted raw and sliced pulse trains resulting from receiving the header portion of the transmitted signal.
Figure 8:
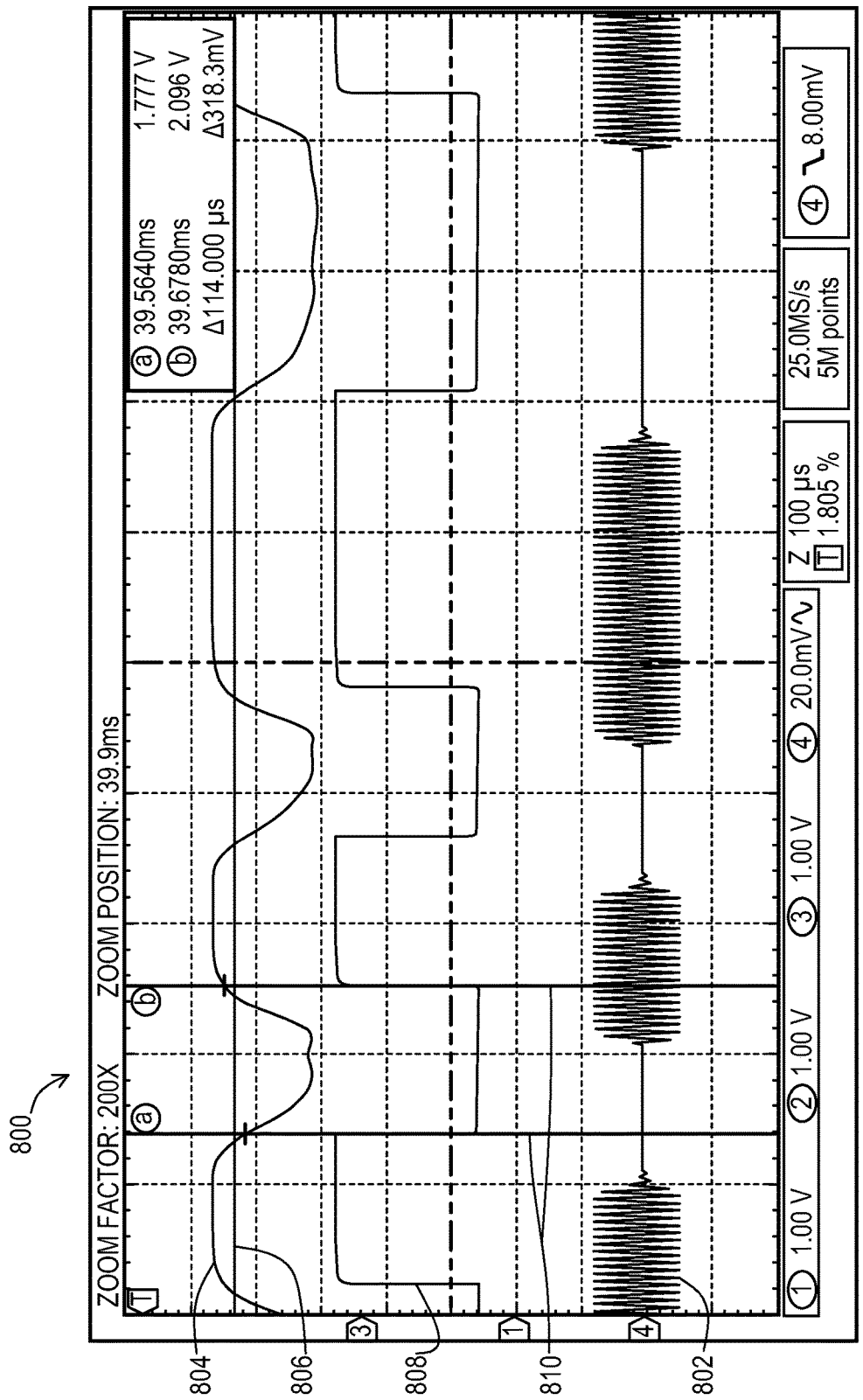
FIG. 8 shows the waveforms from a body portion of a transmitted wireless proximal signal and both undistorted raw and sliced pulse trains resulting from receiving the body portion of the transmitted signal.

As shown in FIG. 7, one way of measuring the pulse width is to make a measurement 710 within the pulse train 708 between the end of the "on" portion of the pulse expected to have a known and fixed width, designated "a," and the beginning of the "on" portion of the subsequent pulse, designated "b." In other words, the "off" portion of the pulse is being measured, i.e. from "a" to "b," rather than the "on" portion. In this example, the header pulse train 702 of the received signal has no distortion and as a result, the measurement 710 is an exact match to the expected "off" time of 57 microseconds. As there is no distortion of the header portion, there is also no distortion of the body portion as shown in FIG. 8, where the measurement 810 from "a" to "b" of 114 microseconds is the correct width of the "off" portion for the particular data rate being used for the body portion.

Figure 6:
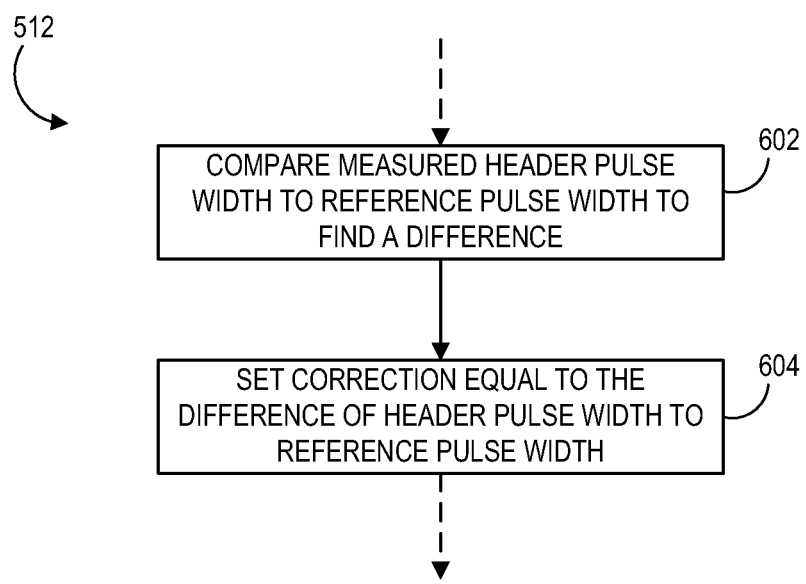
FIG. 6 shows an example of operations that determine and apply the correction within the operations of FIG. 5.

A correction is determined from the measured pulse width difference at an operation 512. As shown in FIG. 6, in one example, the operation 512 involves comparing the pulse width at the reference position to the reference pulse width for that position at an operation 602. The amount by which the pulse width is different from the reference may then be set by the receiving device as a correction value at an operation 604. This correction value is then applied to reduce the "on" portion of the received pulse widths of the body portion when decoding the body portion data at an operation 514.

As discussed above, these operations of FIGS. 5 and 6 may be utilized by either device or both. Where both devices are employing these operations, there is a second wireless signal sent by the device that received the first wireless signal. This signal may occur before or after the signals discussed above while in the same communication session. The second wireless signal is received and a second correction may be determined and applied to correct for any distortion being received by this other device. The second correction may differ from or be the same as the first correction that was determined by the device that has transmitted this signal to this other device, considering the conditions of transmission of this second signal may be different due to a different power level of transmission, differences in the receiving coils of the two devices, and so forth.

Figure 9:
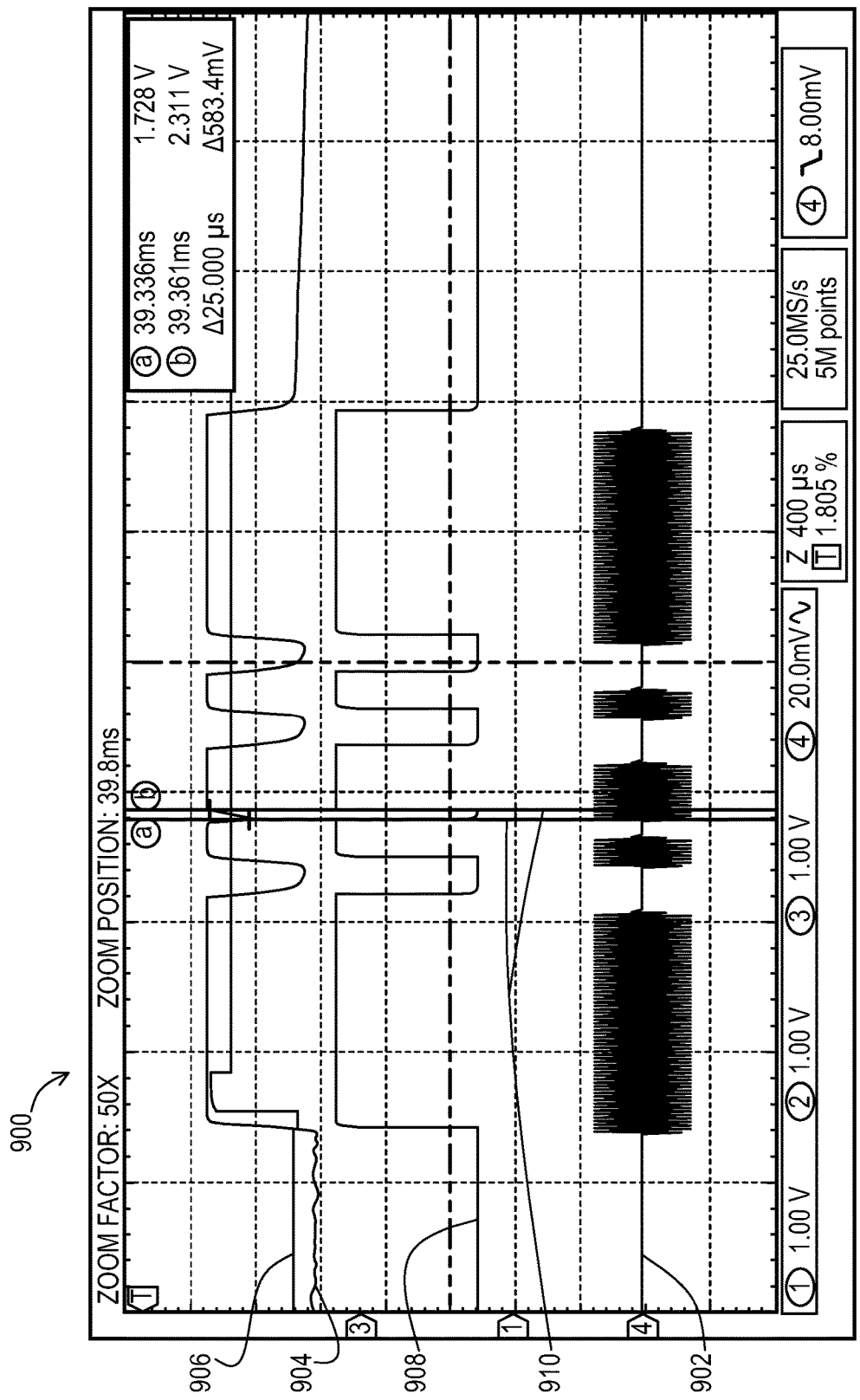
FIG. 9 shows the waveforms from a header portion of a transmitted wireless proximal signal and both distorted raw and sliced pulse trains resulting from receiving the header portion of the transmitted signal that are used to determine a correction.
Figure 10:
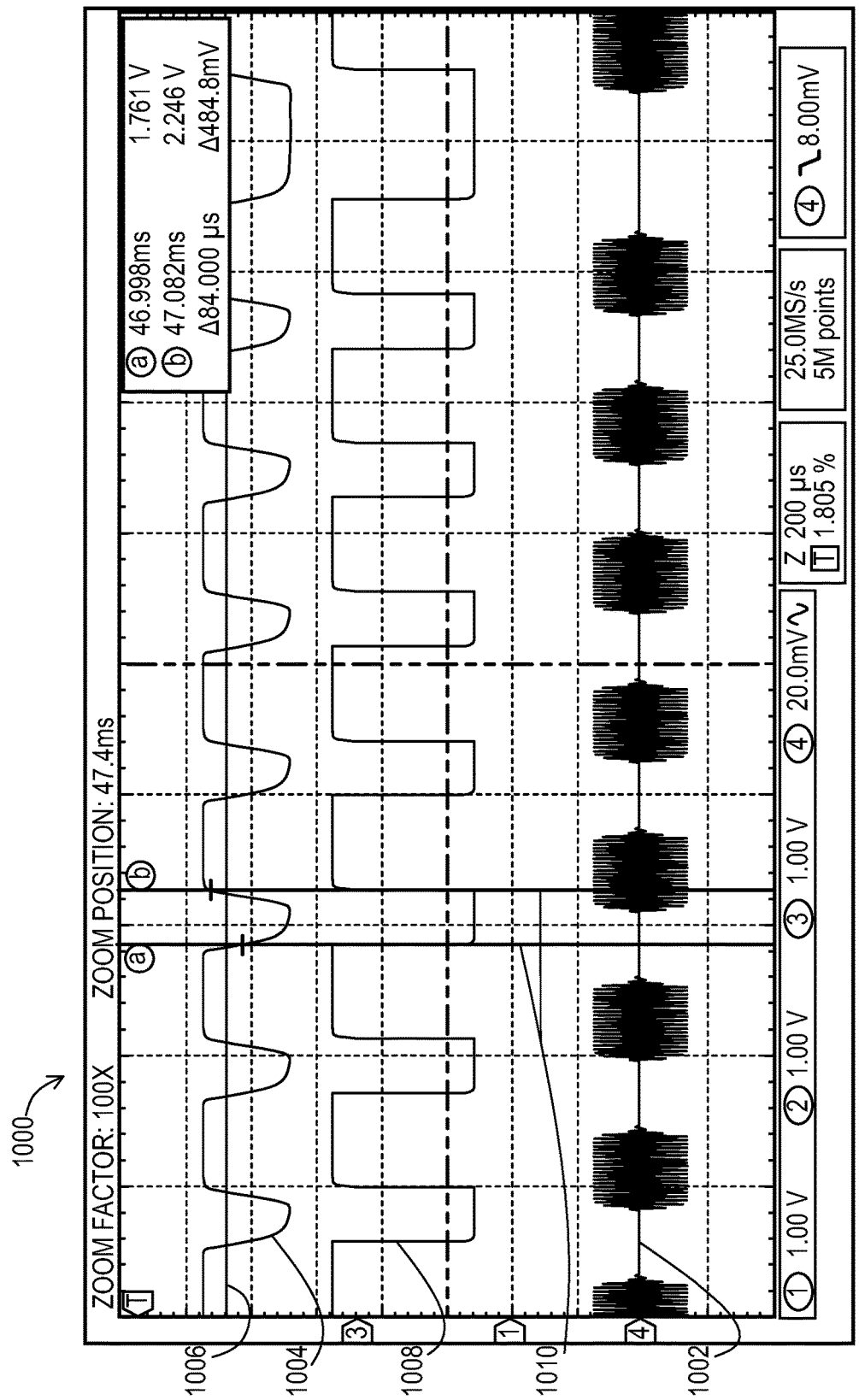
FIG. 10 shows the waveforms from a body portion of a transmitted wireless proximal signal and both distorted raw and sliced pulse trains resulting from receiving the body portion of the transmitted signal where the correction can then be applied to the sliced signal.

FIGS. 9 and 10 illustrate the determination of the correction and how the correction found in the header pulse train also applies to correct the pulses within the body portion pulse train. FIG. 9 shows a waveform diagram 900 where the header portion 902 of the received signal does have distortion. A demodulated pulse train 904 is sliced with the threshold 906 to produce the well defined pulse train 908. A measurement 910 is made between the same points "a" and "b" as was done in the measurement 710 of the pulse train 708 of FIG. 7, but the measurement 910 reveals an "off" width of only 25 microseconds. Since the reference for the "off" time of the pulse in the reference position within the header is 57 microseconds, the receiving device determines from the measurement 910 that there is a distortion of 32 microseconds.

FIG. 10 shows a waveform diagram 1000 where the body portion 1002 is from the same message as the header portion 902 of FIG. 9. Therefore, the body portion 1002 of the received signal also has distortion. A demodulated pulse train 1004 is sliced with the threshold 1006 to produce the well defined pulse train 1008. A measurement 1010 between the same points "a" and "b" which matches the measurement 810 of the pulse train 808 of FIG. 8 shows that the "off" width is only 84 microseconds. Considering the expected "off" width is 114 microseconds, there is an error of 26%. However, because the decoder of the receiving device knows there is a correction of 32 microseconds that should be applied when decoding, the decoder knows to terminate the "on" portion of the pulse 32 microseconds before the actual termination in the pulse train 1008, which results in an "off" width of 116 microseconds, which is only 2 microseconds off from the expected "off" width and is an error of less than 2%, which is trivial to the decoder. Where the protocol is based on width of the pulses, then the correction may alternatively be applied in other manners, such as by delaying the "on" portion of the pulse by 32 microseconds or delaying the "on" portion of the pulse by a first amount and terminating the "on" portion earlier than the actual termination by a second amount where the sum of the first and second amounts is equal to the correction, or 32 microseconds in this example.

Figure 11:
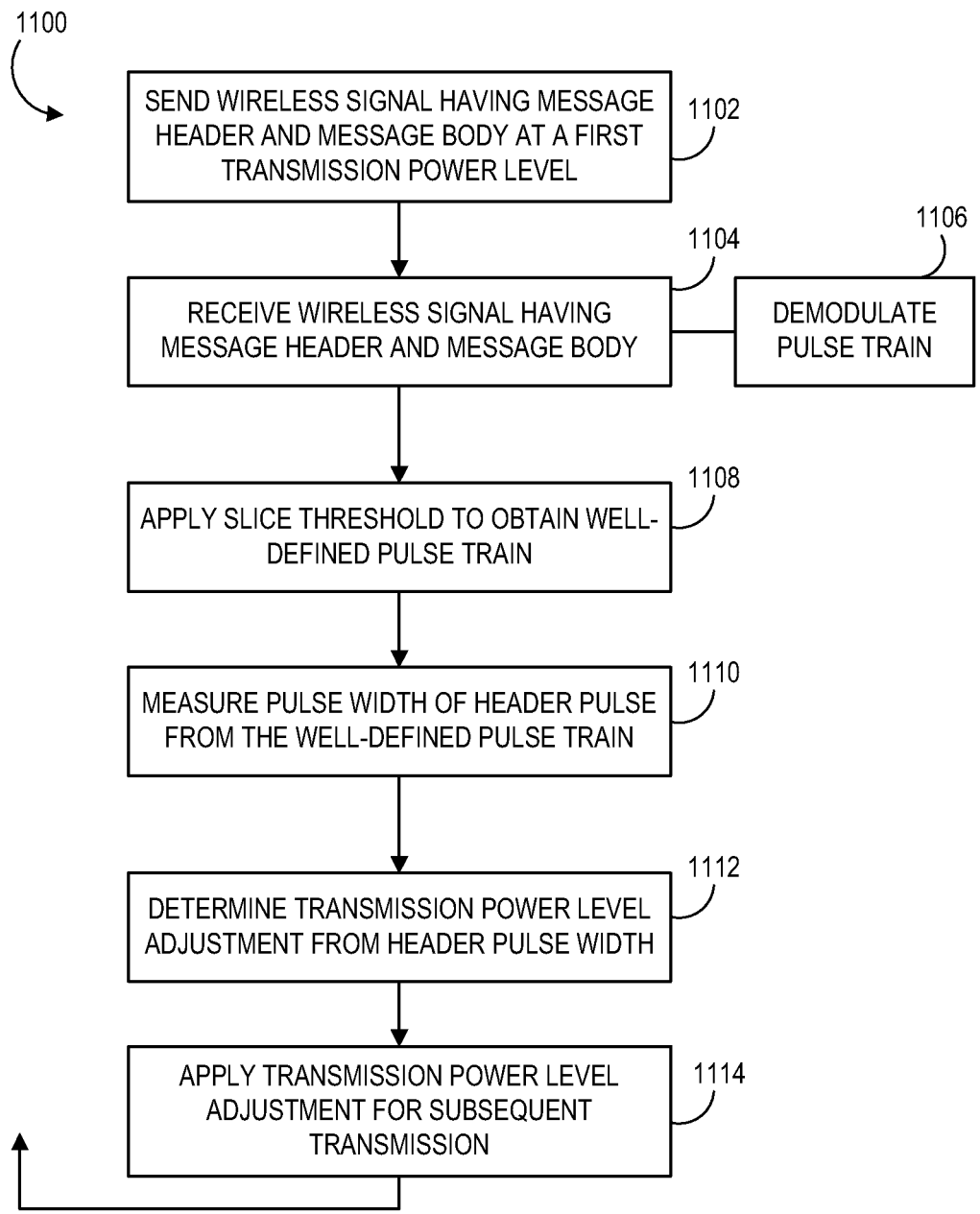
FIG. 11 shows an example of operations that adjusts transmission power level based on distortion in the received signal.

FIG. 11 shows another set 1100 of logical operations that may be performed by either or both devices 102, 104 in order to increase the efficiency of the communication process by reducing the amount of transmission power. When it is determined that distortion is present, this indicates that the transmission power is likely too high and may be reduced.

The operations begin by one device sending a wireless proximal signal to the other device at an operation 1102. The wireless proximal signal is then received at the other device at an operation 1104. The wireless proximal signal of this example also includes a header portion, as shown in FIGS. 7 and 9, and a message body portion as shown in FIGS. 8 and 10.

The header and body portions are demodulated at an operation 1106 as they are being received, and examples of the demodulated pulse trains are shown as header pulse train 704 of FIG. 7 (undistorted example) and 904 of FIG. 9 (distorted example) and body pulse train 804 of FIG. 8 (undistorted example) and 1004 of FIG. 10 (distorted example). The demodulated pulse train is then sliced using the threshold 706, 806, 906, and 1006 at an operation 1108 to produce a well defined pulse train 708, 908 for the header portion and pulse train 808, 1008 for the body portion that is suitable for decoding. As discussed above, any distortion of the received signal like that shown in FIGS. 9 and 10 due to ringing of the receiving coil, which may be caused by the devices being too close together for the power level being used to transmit the signal, will result in the header pulse in the reference position having an "on" time with a greater width than the reference quantity for the "on" time and consequently have an "off" time of less width than the reference quantity for the "off" time. Therefore, at an operation 1110, the receiving device can measure the pulse width of the header pulse in the reference position to then determine if the pulse width, either the "on" time or the "off" time, is the same or different than the reference.

Figure 12:
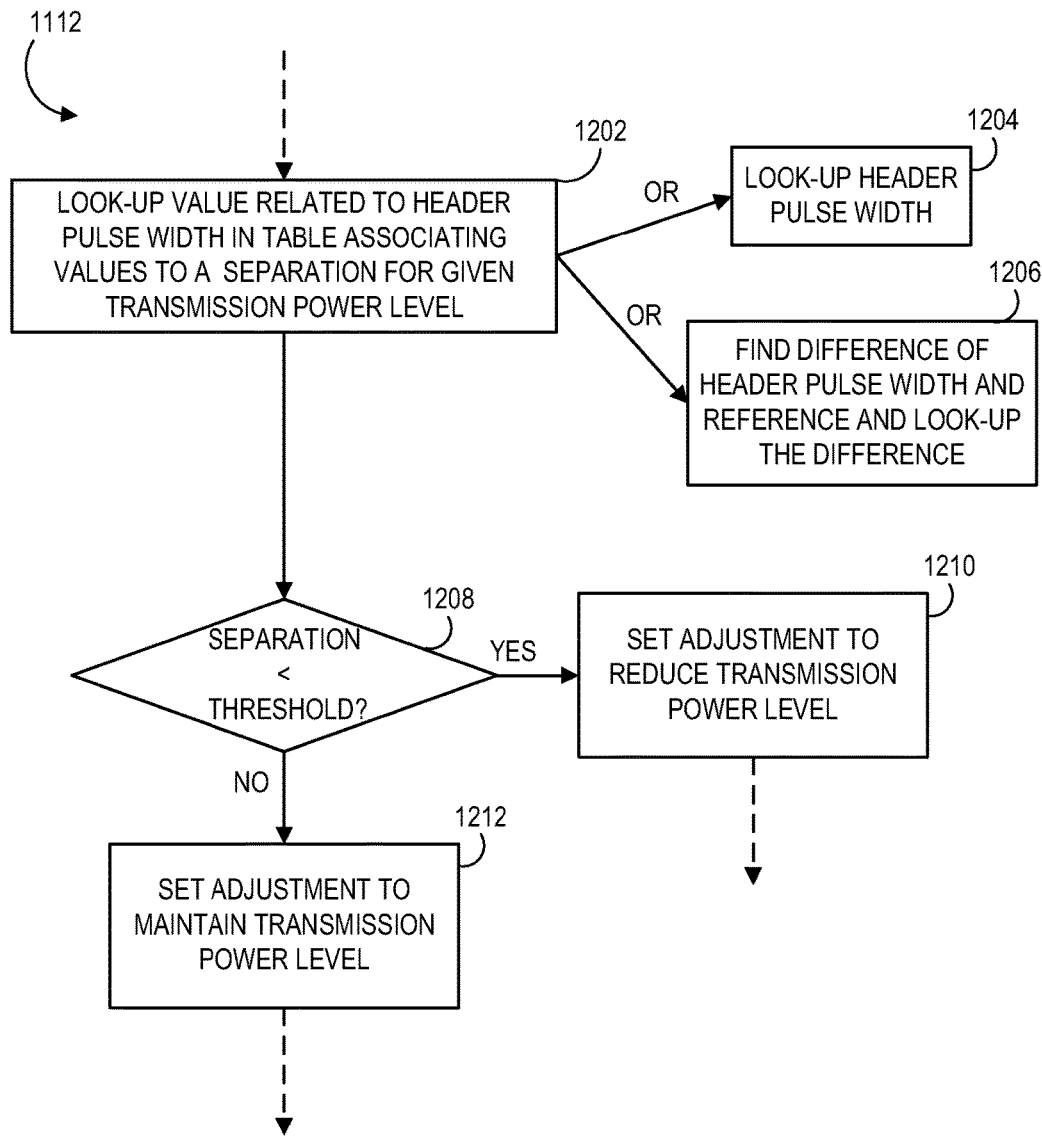
FIG. 12 shows an example of operations that determine and apply the adjustment of the transmission power within the operations of FIG. 11.

An adjustment to the transmission power of the receiving device is then determined from the measured pulse width difference at an operation 1112. As shown in FIG. 12, in one example, the operation 1112 involves performing a look-up within a table of a value related to the pulse width. The table associates pulse width values to a separation distance between devices for a given transmission power level. The table may be constructed from empirical data and stored in memory accessible by the processor of the receiving device. The table may store the actual measured pulse width in association with the separation such that the look-up is of the actual pulse width at a sub-operation 1204. As another example, the table may store the difference between the pulse width and the reference pulse width such that the look-up is of the difference from the reference at a sub-operation 1206.

Once finding the separation from the table, the separation is then compared to a threshold at a query operation 1208. The threshold may also be empirically determined for a given transmission power and may define the separation where the transmission power may be lower than the transmission power level associated with the threshold and still maintain adequate integrity of the communication link. If the separation of the devices is greater than the threshold for the current transmission power level, then the transmission power level is maintained at an operation 1212. If the separation of the devices is less than the threshold for the current transmission power level, then the transmission power level setting is adjusted to a reduced level. The adjusted transmission power level is then applied in subsequent transmissions from the receiving device at an operation 1114 (FIG. 11). Should there be additional separation values and thresholds stored for other transmission power levels, such as the transmission power level that has been achieved after the adjustment of operation 1112, then the operations may repeat to determine if further reductions in transmission power may be done.

Figure 13:
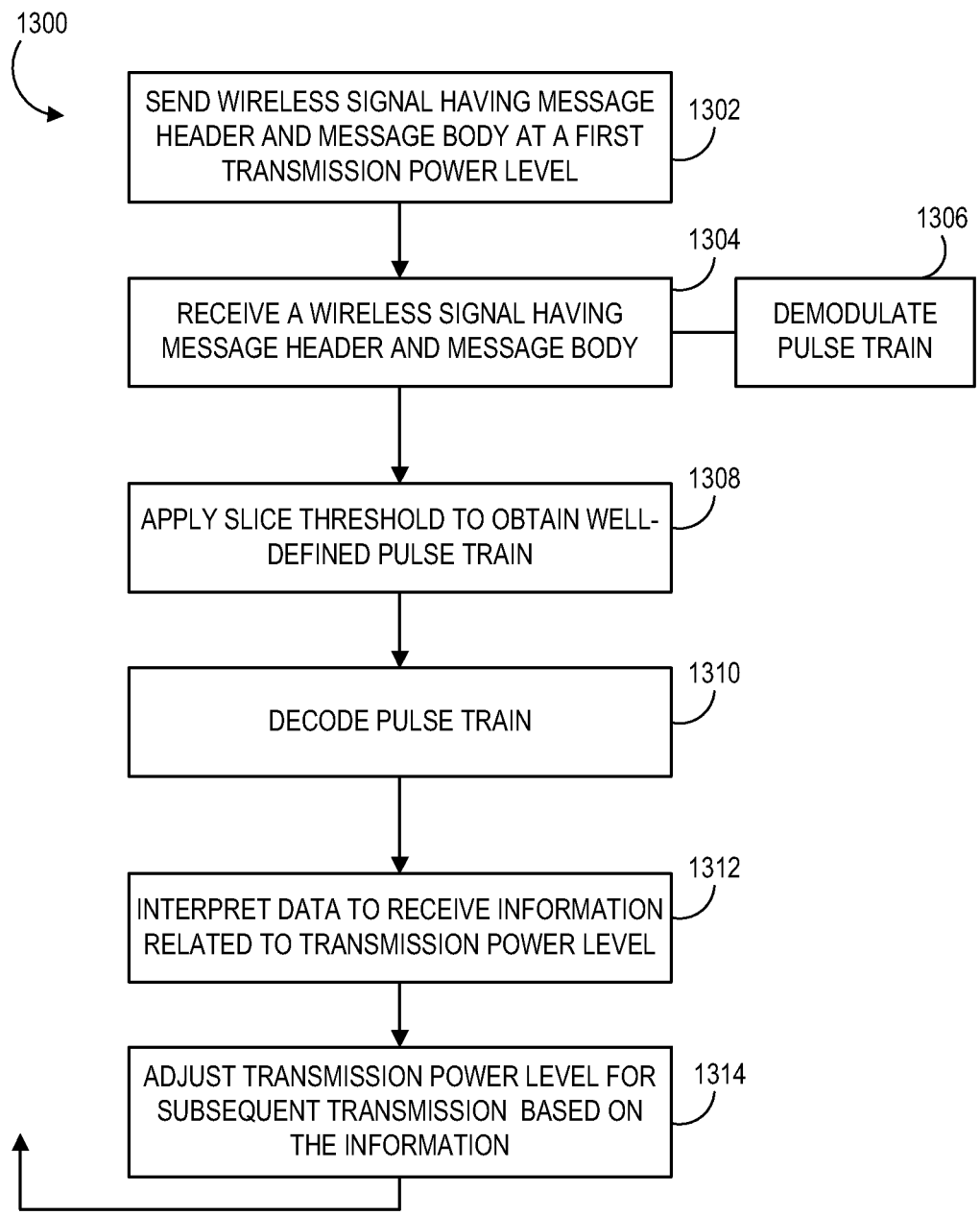
FIG. 13 shows an example of operations that adjusts transmission power level based on received information about distortion in the signal that has been transmitted.
Figure 14:
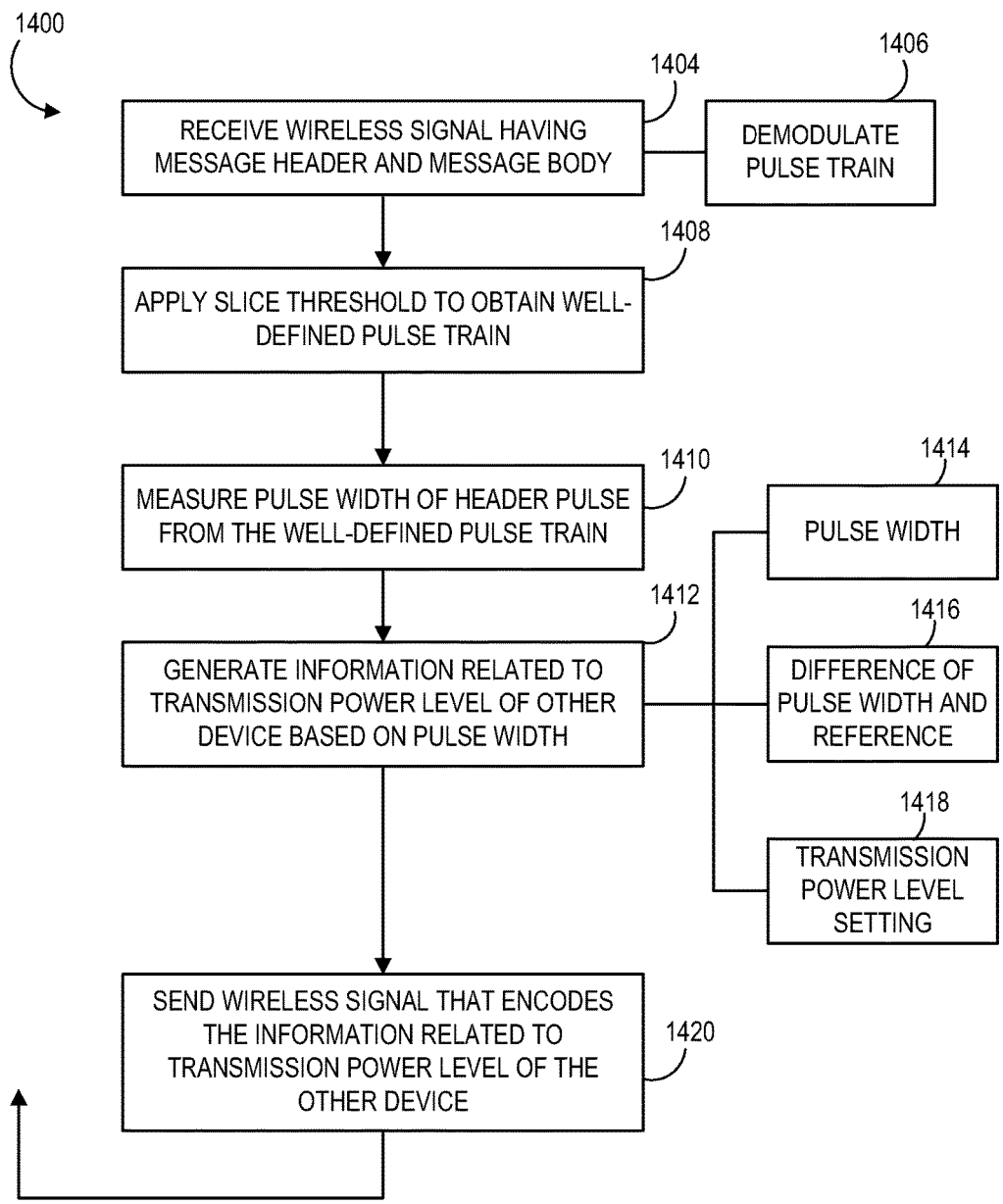
FIG. 14 shows an example of operations that determines an adjustment of transmission power level for another device based on distortion in the signal that has been transmitted by the other device.

FIG. 13 shows another set 1300 of logical operations that may be performed by either or both devices 102, 104 in order to adjust transmission power of the device transmitting the signal that has the distortion. FIG. 14 shows a set 1400 of companion operations performed by the other device.

The set 1300 of operations begin by one device sending a wireless proximal signal to the other device at an operation 1302. The wireless proximal signal is then received at the other device at an operation 1304. The wireless proximal signal of this example also includes a header portion, as shown in FIGS. 7 and 9, and a message body portion as shown in FIGS. 8 and 10.

The header and body portions are demodulated at an operation 1306 as they are being received, and examples of the demodulated pulse trains are shown as header pulse train 704 of FIG. 7 (undistorted example) and 904 of FIG. 9 (distorted example) and body pulse train 804 of FIG. 8 (undistorted example) and 1004 of FIG. 10 (distorted example). The demodulated pulse train is then sliced using the threshold 706, 806, 906, and 1006 at an operation 1308 to produce a well defined pulse train 708, 908 for the header portion and pulse train 808, 1008 for the body portion that is suitable for decoding.

The device receiving these signals may then decode the pulse train at an operation 1310. The decoding at operation 1310 may utilize a measurement of distortion in the received pulse train to find a correction and then apply the correction when decoding, as discussed above in relation to FIGS. 5 and 6. Upon decoding the data, the data is interpreted to receive information that is related to the transmission level of this receiving device at an operation 1312. For example, the data may specify a specific transmission power level to be used by the receiving device when transmitting. As another example, the data may specify the measured distortion, i.e., the difference between the measured pulse width and the reference pulse width, by the other device of the signals being transmitted by this receiving device. As another example, the data may simply specify the pulse width measured by the other device. This device then adjusts the transmission power level for subsequent transmissions based on this information that has been received from the other device at an operation 1314. Similarly, the set 1400 of operations of FIG. 14 begin at an operation 1404 where a wireless proximal signal that has been sent by the device that is designated as the receiving device in the operations of FIG. 13 is received at the other device. The wireless proximal signal of this example also includes a header portion, as shown in FIGS. 7 and 9, and a message body portion as shown in FIGS. 8 and 10.

The header and body portions are demodulated by this other device at an operation 1406 as they are being received, and examples of the demodulated pulse trains are shown as header pulse train 704 of FIG. 7 (undistorted example) and 904 of FIG. 9 (distorted example) and body pulse train 804 of FIG. 8 (undistorted example) and 1004 of FIG. 10 (distorted example). The demodulated pulse train is then sliced using the threshold 706, 806, 906, and 1006 at an operation 1408 to produce a well defined pulse train 708, 908 for the header portion and pulse train 808, 1008 for the body portion that is suitable for decoding.

As discussed above, any distortion of the received signal like that shown in FIGS. 9 and 10 due to ringing of the receiving coil, which may be caused by the devices being too close together for the power level being used to transmit the signal, will result in the header pulse in the reference position having an "on" time with a greater width than the reference quantity for the "on" time and consequently have an "off" time of less width than the reference quantity for the "off" time. Therefore, at an operation 1410, the receiving device can measure the pulse width of the header pulse in the reference position to then determine if the pulse width, either the "on" time or the "off" time, is the same or different than the reference.

An adjustment to the transmission power of the receiving device is then determined by the other device implementing the operations of FIG. 14 from the measured pulse width difference at an operation 1412. The transmission power of this other device implementing the operations of FIG. 14 may also adjust its own transmission power level based on this measured distortion according to the operations of FIGS. 11 and 12. This other device generates information that is related to the transmission power level of the receiving device that is based on the pulse width measurement at an operation 1412. This information may include the pulse width measurement 1414, the difference 1416 between the measured pulse width and the reference pulse width, and/or a specific transmission power level to be used 1418. This other device then sends that information to the receiving device at an operation 1420 so that the receiving device may implement the information as discussed above in relation to FIG. 13.

In this manner, only one of the two devices needs to implement the process of determining a transmission power adjustment. For instance, an external device may implement the process of FIG. 14 and the implantable device then implements the process of FIG. 13 to apply the transmission power adjustment without requiring the overhead of FIG. 14. Likewise, the external device may also implement the process of FIG. so as to adequately control transmission power to thereby eliminate the need for the implantable medical device to employ a correction during decoding as discussed in the prior examples.

Figure 15:
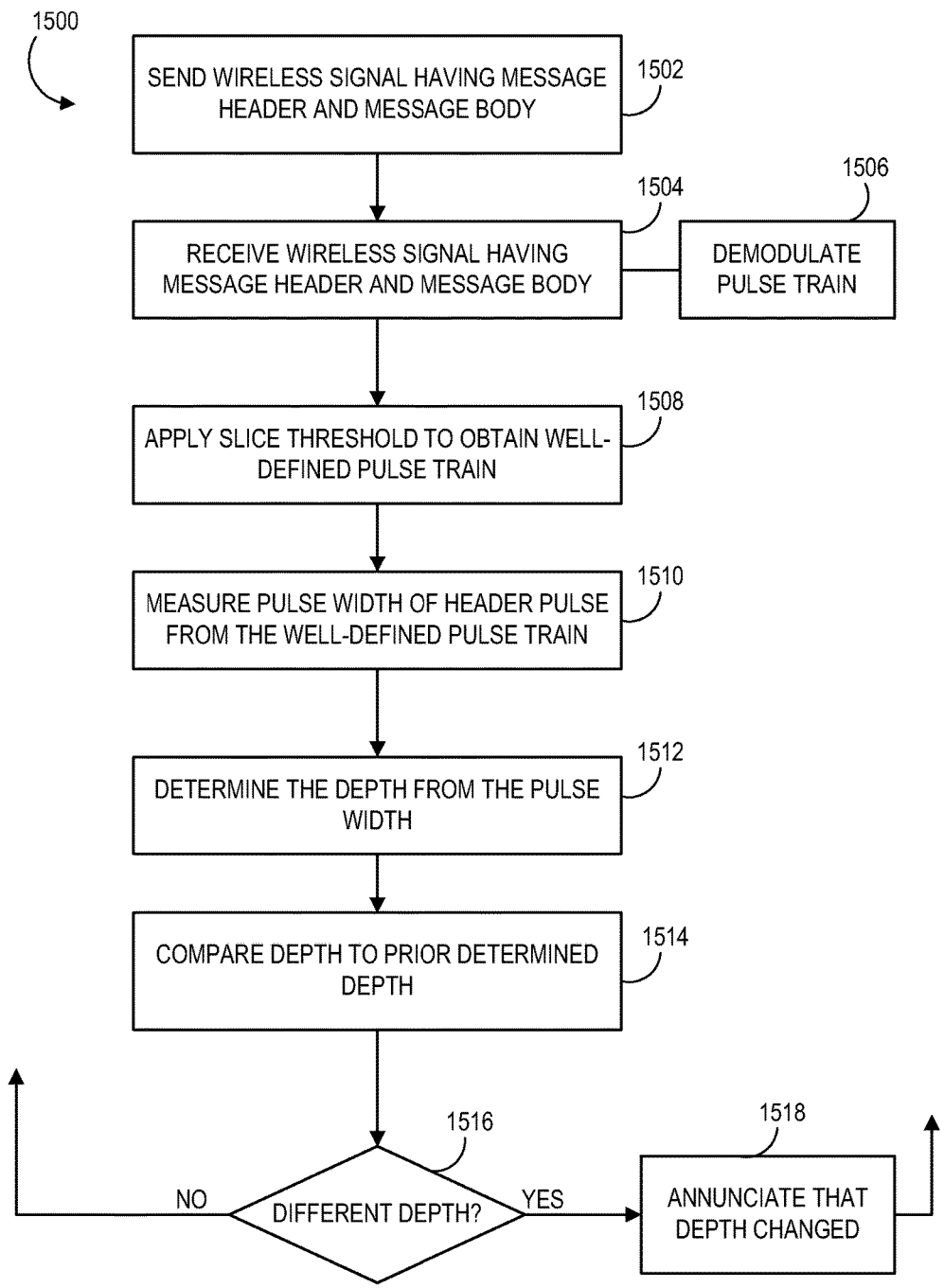
FIG. 15 shows an example of operations that utilizes a depth determination of an implanted device based on distortion in a received signal to signal depth migration.

FIG. 15 shows another set 1500 of logical operations that may be performed by an external device 102 in order to determine a depth of the implanted device 104 within the patient 112. Any change in the depth from a previously known depth of the device 104 indicates that the device 104 is migrating. The clinician may then need to consider whether further intervention is necessary to prevent any complications or other issues that may result from such migration.

The operations begin by the implanted device 104 sending a wireless proximal signal to the external device 102 at an operation 1502 while the telemetry head 106 is held at a reference distance from the patient 112. The wireless proximal signal is then received at the external device 102 at an operation 1504. The wireless proximal signal of this example also includes a header portion, as shown in FIGS. 7 and 9, and a message body portion as shown in FIGS. 8 and 10.

The header and body portions are demodulated by the external device 102 at an operation 1506 as they are being received, and examples of the demodulated pulse trains are shown as header pulse train 704 of FIG. 7 (undistorted example) and 904 of FIG. 9 (distorted example) and body pulse train 804 of FIG. 8 (undistorted example) and 1004 of FIG. 10 (distorted example). The demodulated pulse train is then sliced using the threshold 706, 806, 906, and 1006 at an operation 1508 to produce a well defined pulse train 708, 908 for the header portion and pulse train 808, 1008 for the body portion that is suitable for decoding.

As discussed above, any distortion of the received signal like that shown in FIGS. 9 and 10 due to ringing of the receiving coil, which may be caused by the devices being too close together for the power level being used to transmit the signal, will result in the header pulse in the reference position having an "on" time with a greater width than the reference quantity for the "on" time and consequently have an "off" time of less width than the reference quantity for the "off" time. Therefore, at an operation 1510, the receiving device can measure the pulse width of the header pulse in the reference position to then determine if the pulse width, either the "on" time or the "off" time, is the same or different than the reference.

Figure 16:
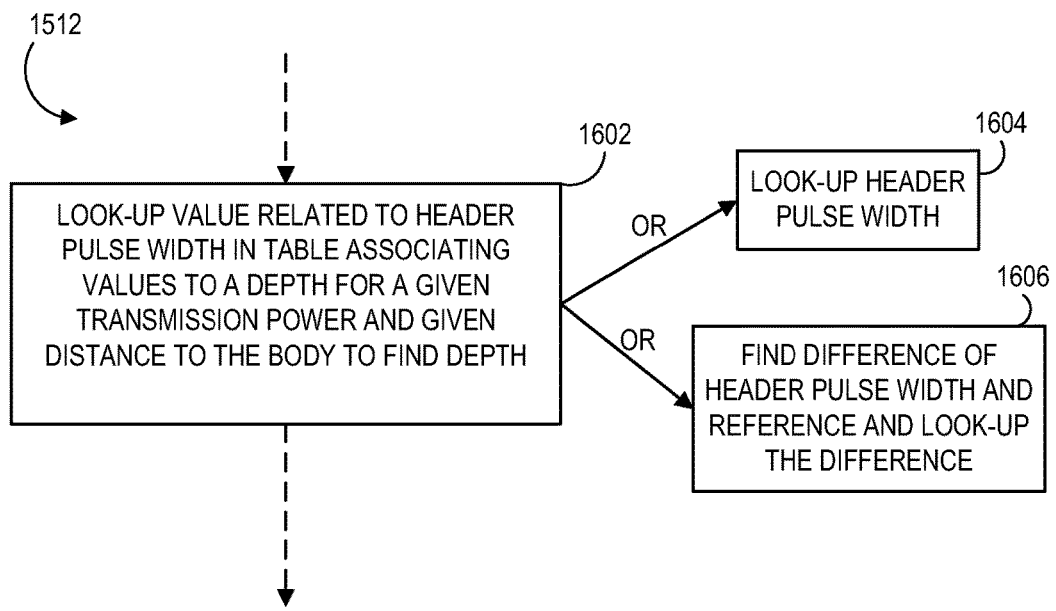
FIG. 16 shows an example of operations that determine the depth of the implanted device within the operations of FIG. 15.

A depth of the implanted device 104 is then determined from the measured pulse width difference at an operation 1512. As shown in FIG. 16, in one example, the external device 102 determines the depth by performing a look-up of a value related to the measured pulse width in a table stored by the external device 102 at an operation 1602. The look-up finds a depth associated to that value for a given transmission power level and reference distance of the telemetry head from the body of the patient 112. These depths in the table may be determined empirically. In one example, the telemetry head may always be placed directly on the body of the patient and directly over the implanted device, the location of which being determined by palpitation, and in that case, the reference distance is always zero. Also, the value that is associated with the depth and that is related to the measured pulse width may be the actual measured pulse width 1604 or the difference 1606 between the measured pulse width and the reference pulse width.

The external device 102 may then present that depth to the user via an audible and/or visual message at the operation 1512 upon finding the depth from the table. The external device 102 may additionally or alternatively perform additional operations including a comparison of the currently determined depth to a stored depth determined in a previous communication session, e.g., at a prior visit by the patient to a clinician or at a prior self-conducted communication session by the patient using an external device 102, at an operation 1514. At a query operation 1516, the external device 102 detects whether the current depth is different than the prior depth. If the depth is different, then external device 102 may then annunciate to the user via an audible and/or visible message that the device depth has changed at an operation 1518.

Figure 17:
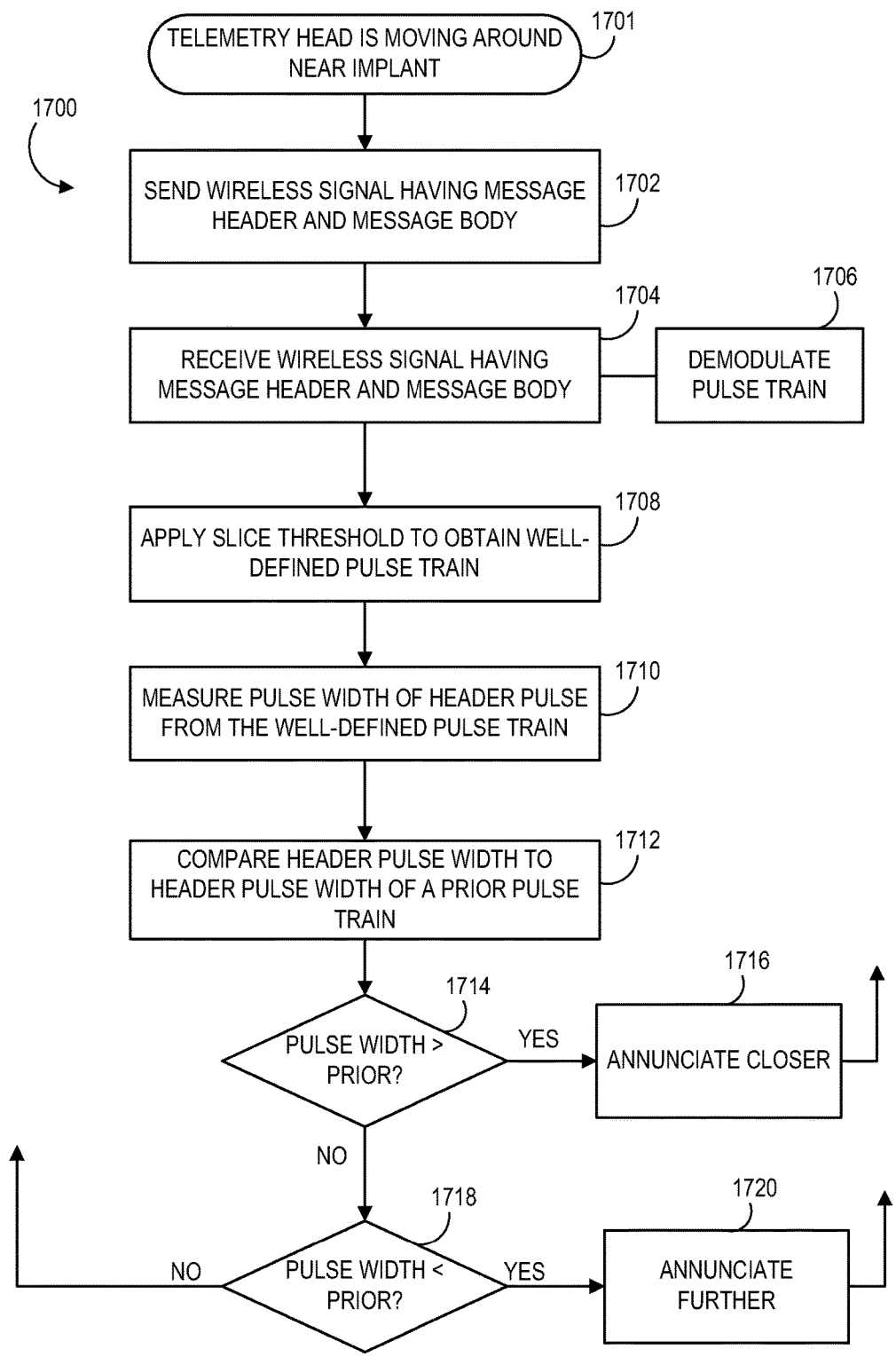
FIG. 17 shows an example of operations that signals device location based on distortion in a received signal.

FIG. 17 shows another set 1700 of logical operations that may be performed by an external device 102 in order to determine a location of the implanted device 104 within the patient 112. Any change in the location from a previously known location of the device 104 also indicates that the device 104 is migrating. Furthermore, knowing the location of the device allows the telemetry head 106 to be placed in a position to make the wireless proximal communications occur as efficiently and accurately as possible. For the long term, the clinician may need to consider whether further intervention is necessary to prevent any complications or other issues that may result from such migration. In the short term, the clinician can place the telemetry head 106 directly over the implanted device 104 to optimize wireless proximal communications upon determining the precise location of that device 104.

Initially, the user is moving the telemetry head 106 around in the general area of the implanted device 104 while attempting to maintain a fixed distance of the telemetry head 106 to the body 112. During this movement, the operations proceed by the implanted device 104 sending a wireless proximal signal to the external device 102 at an operation 1702. The wireless proximal signal is then received at the external device 102 at an operation 1704. The wireless proximal signal of this example also includes a header portion, as shown in FIGS. 7 and 9, and a message body portion as shown in FIGS. 8 and 10.

The header and body portions are demodulated by the external device 102 at an operation 1706 as they are being received, and examples of the demodulated pulse trains are shown as header pulse train 704 of FIG. 7 (undistorted example) and 904 of FIG. 9 (distorted example) and body pulse train 804 of FIG. 8 (undistorted example) and 1004 of FIG. 10 (distorted example). The demodulated pulse train is then sliced using the threshold 706, 806, 906, and 1006 at an operation 1508 to produce a well defined pulse train 708, 908 for the header portion and pulse train 808, 1008 for the body portion that is suitable for decoding.

As discussed above, any distortion of the received signal like that shown in FIGS. 9 and 10 due to ringing of the receiving coil, which may be caused by the devices being too close together for the power level being used to transmit the signal, will result in the header pulse in the reference position having an "on" time with a greater width than the reference quantity for the "on" time and consequently have an "off" time of less width than the reference quantity for the "off" time. Therefore, at an operation 1710, the external device 102 can measure the pulse width of the header pulse in the reference position to then determine if the pulse width, either the "on" time or the "off" time, is the same or different than the reference.

The location of the implanted device 104 is then suggested based on a comparison of the currently measured pulse width relative to that of a prior pulse width, such as a pulse width from a prior message, at an operation 1712. The external device 102 detects whether the current pulse width is wider than a prior pulse width at a query operation 1714. If so, then that means that there is an increase in distortion so the telemetry head 106 must be closer to the location of the implanted device 104 since the distance of the telemetry head 106 to the body 112 is being maintained by the user while moving the telemetry head 106 during these operations. Therefore, the external device 102 annunciates via an audible and/or visual signal that the telemetry head 106 is closer to the implanted device 104 than immediately prior at an operation 1716. For example, the external device 102 may provide a series of beeping sounds and the interval between the beeps may get shorter to indicate that the telemetry head 106 is closer to the implanted device 104, similar to how a metal detector signals the user that the metal detector is closer to a metal object. If the pulse width is less than a prior pulse width as detected at a query operation 1718, then that means that there is a decrease in distortion so the telemetry head 106 must be further from the location of the implanted device 104. In that case, the external device 102 may provide an audible and/or visible annunciation that the telemetry head 106 has moved further away from the implanted device 104 at an operation 1720.

While embodiments have been particularly shown and described, it will be understood by those skilled in the art that various other changes in the form and details may be made therein without departing from the spirit and scope of the invention.

What is claimed is:

1. A method of exchanging wireless proximal communications, comprising:
   receiving at a first device a wireless signal that includes a header portion representing header data and a body portion representing body data;
   obtaining header pulses representative of the header data and body pulses representative of the body data from the received wireless signal, where the header pulses have a header pulse width and the body pulses have a body pulse width;
   determining a correction by comparing at the first device the header pulse width to a reference pulse width that is different than the body pulse width to find a difference between the header pulse width and the reference pulse width and wherein the correction is based on the difference;
   decoding the data represented by the body pulses by applying the correction at the first device; and
   controlling the first device with the decoded data.

2. The method of claim 1, wherein the correction is equal to the difference.

3. The method of claim 2, wherein the difference is a first amount of time and the correction is equal to the first amount of time.

4. The method of claim 2, wherein the reference pulse width corresponds to a 50% duty cycle of a period of the header pulses.

5. The method of claim 1 further comprising:
   sending a second wireless signal from the first device to a second device;
   receiving at the second device the second wireless signal sent by the first device that includes a header portion and a body portion;
   obtaining at the second device header pulses representative of the header data and body pulses representative of the body data from the received second wireless signal, where the header pulses from the second wireless signal have a header pulse width and the body pulses from the second wireless signal have a body pulse width;
   determining a second correction based on the header pulse width from the second wireless signal; and
   applying at the second device the second correction when decoding the data represented by the body pulses of the second wireless signal.

6. The method of claim 5, wherein determining the second correction comprises comparing at the second device the header pulse width of the header pulses from the second wireless signal to a reference pulse width to find a second difference between the header pulse width from the second wireless signal and the reference pulse width, and wherein applying at the second device the second correction comprises applying the second correction based on the second difference.

7. The method of claim 1, wherein the wireless signal includes a set of instructions, the method further comprising providing electrical stimulation therapy to a patient in accordance with the set of instructions received via the wireless signal.

8. A device for exchanging wireless proximal communications, comprising:
   a receiving circuit that is configured to receive and demodulate a wireless signal that includes a header portion and that includes a body portion that represents body data to produce a demodulated signal of the header portion and the body portion; and
   a processor that converts the demodulated signal to header pulses of the header portion and body pulses of the body portion with the header pulses having a header pulse width and the body pulses having a body pulse width, determines a correction by comparing the header pulse width to a reference pulse width contained at the device that is different than the body pulse width to find a difference between the header pulse width and the reference pulse width wherein the correction is based on the difference, decodes the body data by applying the correction and controls the device with the decoded body data.

9. The device of claim 8, wherein the processor contains the reference pulse width.

10. The device of claim 9, wherein the difference is a first amount of time and the correction is equal to the first amount of time.

11. The device of claim 9, wherein the reference pulse width corresponds to a 50% duty cycle of a period of the header pulses.

12. The device of claim 8, wherein the wireless signal represents a set of instructions, the device further comprising an electrical stimulation circuit and wherein the processor controls operation of the electrical stimulation circuit based on the set of instructions received from the body data decoded from the pulses obtained from the wireless signal.

13. A system for exchanging wireless proximal communications, comprising:
   a first device that comprises:
      a receiving circuit that receives and demodulates a first wireless signal that includes a header portion and that includes a body portion that represents body data to produce a demodulated signal of the header portion and the body portion;
a processor that converts the demodulated signal to header pulses of the header portion and body pulses of the body portion with the header pulses of the header portion having a header pulse width and with the body pulses of the body portion having a body pulse width, determines a correction by comparing the header pulse width to a reference pulse width contained at the first device that is different than the body pulse width to find a difference between the header pulse width and the reference pulse width where the correction is based on the difference, decodes the body data from the pulses of the body portion by applying the first correction, and controls operation of the first device with the decoded body data from the first wireless signal; and
a transmitter circuit that transmits a second wireless signal;
the system further comprising a second device that comprises:
a receiving circuit that receives and demodulates the second wireless signal that includes a header portion and that includes a body portion to produce a demodulated signal of the header portion and the body portion;
a processor that converts the demodulated signal to pulses of the header portion and the body portion of the second wireless signal with the pulses having a pulse width, determines a second correction based on the header pulse width of the second wireless signal, decodes body data from the body pulses of the body portion of the second wireless signal by applying the second correction, and controls operation of the second device with the decoded body data from the second wireless signal; and
a transmitter circuit that transmits the first wireless signal.

14. The system of claim 13, wherein the processor of the first device contains the reference pulse width.

15. The system of claim 14, wherein the difference is a first amount of time and the correction is equal to the first amount of time.

16. The system of claim 14, wherein the reference pulse width corresponds to a 50% duty cycle of a period of the header pulses.

17. The system of claim 13, wherein the first wireless signal includes a set of instructions, wherein the first device further comprises an electrical stimulation circuit and wherein the processor controls operation of the electrical stimulation circuit based on the set of instructions received from the body data decoded from the pulses obtained from the first wireless signal.

18. A method of exchanging wireless proximal communications, comprising:
receiving at a first device a wireless signal that includes a header portion representing header data and a body portion representing body data;
obtaining header pulses representative of the header data and body pulses representative of the body data from the received wireless signal, where the header pulses have a header pulse width and the body pulses have a body pulse width;
determining a correction based on the header pulse width;
decoding the data represented by the body pulses by applying at the first device the correction; wherein determining the correction comprises comparing at the first device the header pulse width to a reference pulse width to find a difference between the header pulse width and the reference pulse width and wherein the correction is based on the difference and wherein the difference is a first amount of time and the correction is equal to the first amount of time; and
controlling the first device with the decoded data.

19. A device for exchanging wireless proximal communications, comprising:
a receiving circuit that is configured to receive and demodulate a wireless signal that includes a header portion and that includes a body portion that represents body data to produce a demodulated signal of the header portion and the body portion; and
a processor that converts the demodulated signal to header pulses of the header portion and body pulses of the body portion with the header pulses having a header pulse width and the body pulses having a body pulse width, determines a correction based on the header pulse width, decodes the body data by applying the correction; and controls the device with the decoded data, wherein the processor contains a reference pulse width and compares the header pulse width to the reference pulse width to find a difference between the header pulse width and the reference pulse width and applies the correction based on the difference to the body pulses when decoding the body data, and wherein the difference is a first amount of time and the correction is equal to the first amount of time.

20. A system for exchanging wireless proximal communications, comprising:
a first device that comprises:
a receiving circuit that receives and demodulates a first wireless signal that includes a header portion and that includes a body portion that represents body data to produce a demodulated signal of the header portion and the body portion;
a processor that converts the demodulated signal to header pulses of the header portion and body pulses of the body portion with the header pulses having a header pulse width and the body pulses having a body pulse width, determines a correction based on the header pulse width, decodes the body data from the body pulses from the body portion of the first wireless signal by applying the correction, and controls the first device with the decoded data of the first wireless signal; and
a transmitter circuit that transmits a second wireless signal;
the system further comprising a second device that comprises:
a receiving circuit that receives and demodulates the second wireless signal that includes a header portion and that includes a body portion to produce a demodulated signal of the header portion and the body portion;
a processor that converts the demodulated signal to header pulses of the header portion and body pulses of the body portion of the second wireless signal with the header pulses having a header pulse width and the body pulses having a body pulse width, determines a second correction based on the header pulse width of the second wireless signal, decodes body data from the body pulses of the body portion of the second wireless signal by applying the second correction, and controls the second device with the decoded data of the second wireless signal; and a transmitter circuit that transmits the first wireless signal, wherein the processor of the first device contains a reference pulse width and compares the header pulse width from the first wireless signal to the reference pulse width to find a difference between the header pulse width and the reference pulse width and applies the correction based on the difference to the body pulses when decoding the body data, and wherein the difference is a first amount of time and the correction is equal to the first amount of time.

* * * * *